United States Patent
Jeanbourquin

(10) Patent No.: US 6,223,936 B1
(45) Date of Patent: May 1, 2001

(54) DEVICE FOR DISPENSING FLUIDS

(75) Inventor: Edgar Jeanbourquin, Neuendorf (CH)

(73) Assignee: Disetronic Licensing AG, Bergdorf (CH)

( * ) Notice: Subject to any disclaimer, the term of this patent is extended or adjusted under 35 U.S.C. 154(b) by 0 days.

(21) Appl. No.: 09/380,807

(22) PCT Filed: Mar. 10, 1997

(86) PCT No.: PCT/CH97/00092

§ 371 Date: Nov. 15, 1999

§ 102(e) Date: Nov. 15, 1999

(87) PCT Pub. No.: WO98/40115

PCT Pub. Date: Sep. 17, 1998

(51) Int. Cl.[7] .................................................... B67D 5/62
(52) U.S. Cl. ............................ 222/1; 222/327; 222/340; 222/386; 222/137; 604/82; 604/191
(58) Field of Search ............................ 222/1, 327, 340, 222/386, 391, 137, 309; 604/82, 191

(56) References Cited

U.S. PATENT DOCUMENTS

| | | | |
|---|---|---|---|
| 2,556,980 | * 6/1951 | Raedecke | 222/340 X |
| 3,782,598 | * 1/1974 | Basa | 222/340 X |
| 4,214,584 | 7/1980 | Smirnov. | |
| 4,865,229 | * 9/1989 | Schneider et al. | 222/340 X |
| 4,874,368 | 10/1989 | Miller. | |
| 4,957,223 | * 9/1990 | Beilush | 222/340 |
| 5,046,642 | * 9/1991 | Cathcart, Sr. et al. | 222/340 X |
| 5,137,181 | 8/1992 | Keller. | |
| 5,788,673 | 8/1998 | Young. | |
| 5,875,928 | * 3/1999 | Muller et al. | 222/137 X |
| 5,881,928 | * 3/1999 | Register et al. | 222/340 |
| 5,975,367 | * 11/1999 | Coelho et al. | 222/137 |
| 6,047,861 | * 4/2000 | Vidal et al. | 222/137 |
| 6,090,080 | 7/2000 | Jost. | |

FOREIGN PATENT DOCUMENTS

| | | |
|---|---|---|
| 0045339 | 2/1982 | (EP). |
| 0435512 | 7/1991 | (EP). |
| 0513128 | 11/1992 | (EP). |
| WO8505275 | 12/1985 | (WO). |
| WO9306940 | 4/1993 | (WO). |

* cited by examiner

Primary Examiner—Kenneth Bomberg
(74) Attorney, Agent, or Firm—Dorsey & Whitney LLP

(57) ABSTRACT

The invention relates to a dispensing device for simultaneously dispensing fluid from at least two fluid containers fitted with plungers, wherein the device includes an actuating device having at least two output elements, a push element able to displace the output elements, a force element that acts on the push element in the direction of the fluid containers, and a brake element which acts on the push element and can be manually modified to cancel the effect of the force element.

26 Claims, 2 Drawing Sheets

DEVICE FOR DISPENSING FLUIDS

PRIORITY

This is a national stage Application of PCT Application No. PCT/CH97/00092, filed Mar. 10, 1997.

FIELD OF THE INVENTION

The invention relates to a fluid delivery device for simultaneously delivering fluids from at least two fluid containers.

BACKGROUND

Automatic fluid delivery devices are well known. Typically, a force acts on a container holding a fluid so that the fluid, which is usually highly viscous, e.g., pastes, oils, medicaments, and the like, is disposed out of an end of the container. A spring or gas is typically used to supply the force acting on the container.

Known from patent EP-B-0 435 512 is a medicament delivery device in which a spring provided in the interior of a container directly acts on a plunger which separates the spring portion from the medicament portion. Due to the force of the spring the plunger is pushed into the medicament portion to dispel the medicament. Through an infusion tube the medicament is transported to the treatment site in the human body. The flow of the medicament is opened and closed by a clamp attached to the infusion tube. Any other way of closing off the medicament flow is achievable only at significantly greater expense.

U.S. Pat. No. 4,874,368, and PCT application WO 93/06940 describe delivery devices which deliver fluids from two containers arranged in parallel. The containers each have a movable plunger on one end, and an orifice on the other. Each plunger is connected to a plunger rod, the rods being held by a cover containing them. By manually moving the cover in the direction of the contained materials, the two plungers are pushed uniformly in the direction of the contained materials, disposing the materials out of the containers through the orifices. A dual cannula is fitted to the two orifices of the containers, and acts to mix the two materials upon discharge.

The disadvantage of these known devices is that the force for delivering the fluids dispensed needs to be applied either manually or, where automatic fluid delivery is involved, the device is insufficient for a dispensed delivery.

SUMMARY

The invention is intended to provide a solution to the above described problems. The invention is based on the object of developing a fluid delivery device which displaces fluid from at least two containers by means of a spring actuator, including a simple device for metering delivery and which is inexpensive to manufacture.

The invention achieves the cited object by a delivery device which comprises the at least two fluid containers, each fluid container having a plunger and a plunger rod, a pushing element that moves the plunger rods in the direction of the fluid containers under the guidance of a force element, and a brake element that acts on the pushing element and can counteract the force of the force element and can be deactivated manually.

One advantage of the invention is to permit metered delivery of the fluids to be mixed from two or more containers by means of an inexpensive automatic delivery device.

DETAILED DESCRIPTION

In the following description the terms proximal and distal as used in medical terminology are employed, i.e. proximal=facing the patient and distal=facing away from the patient.

Figure 1:
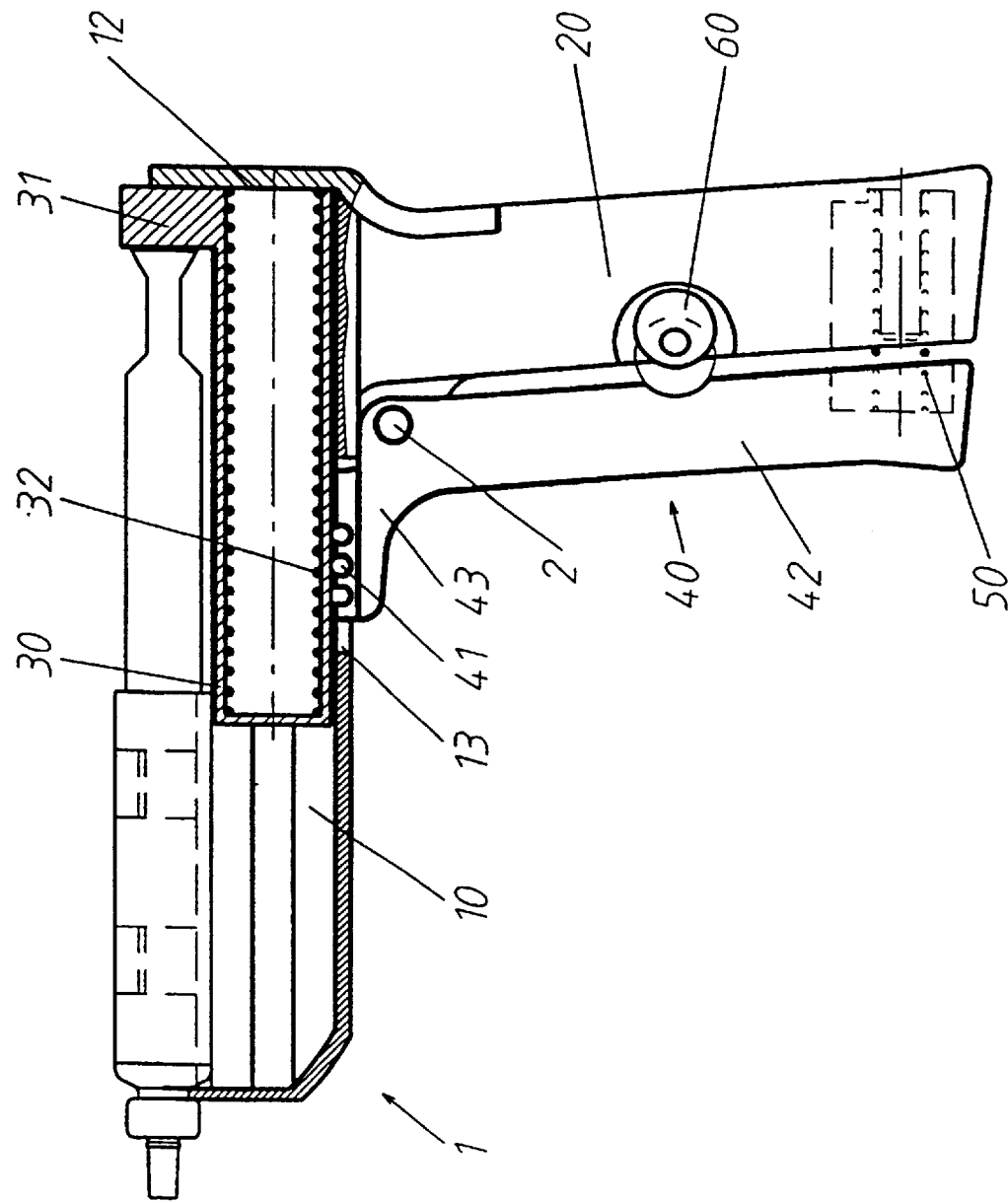
FIG. 1 is a side view of one embodiment of a device in accordance with the present invention.
Figure 2:
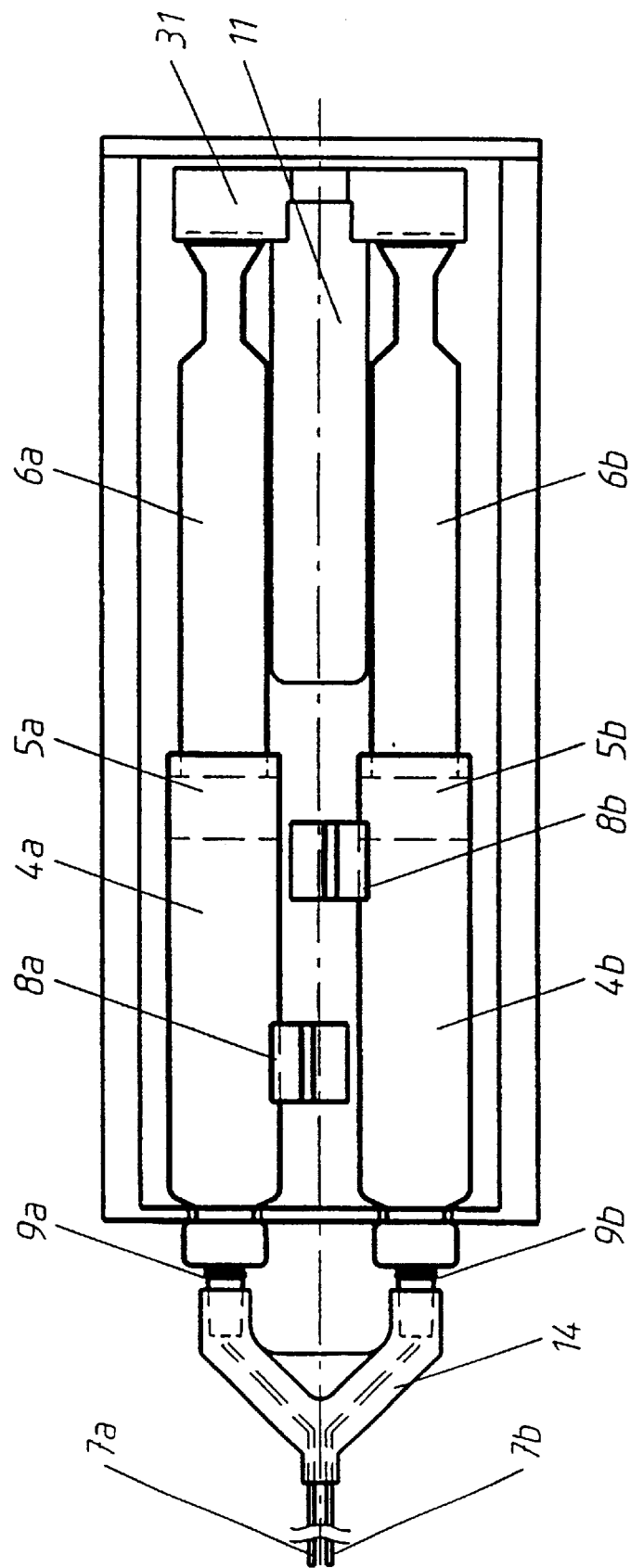
FIG. 2 is a top view of the embodiment of the present invention shown in FIG. 1.

Referring now to FIGS. 1 and 2 it is evident that the delivery device in accordance with one embodiment of the invention comprises a pistol-type housing 1 made up of two main elements, an actuator and a grip 20. In one embodiment, the actuator is a hollow carrier 10. In the transition between the grip 20 and the carrier 10 a spindle 2 is arranged which carries a brake lever 40. The user operates the delivery device 1 like a pistol.

Arranged in parallel on the carrier 10 are two fluid containers. In one embodiment, the fluid containers can be syringe bodies 4a, 4b. The two syringe bodies are immovably held in place by two fixtures 8a, 8b on the surface of the carrier 10. Contained in the syringe bodies 4a, 4b are the two fluids to be mixed. Syringe bodies are substantially hollow-cylindrical containers 4a, 4b closed off at the distal end by a movable plunger 5a, 5b and at the proximal end by an outlet member 9a, 9b. Each plunger 5a, 5b is equipped with an output element. In one embodiment, the element can be a plunger rod 6a, 6b to extend its length. Fitted to each outlet opening 9a, 9b is a cannula 7a, 7b such that mixing of the two fluids does not take place until at the site to which the two fluids are applied. In this arrangement the two cannulas 7a, 7b may be held in a supporting housing 14. Instead of a housing 14 supporting the cannulas 7a, 7b a squirter may also be employed which squirts the two fluids to be mixed onto a surface area.

Located in the interior of the hollow carrier 10 is a push element. In one embodiment, the push element can be a slider 30 on which a force element acts. In one embodiment, the force element is a spring. The spring arranged in the distal portion of the mount 10 acts such that the slider 30 is displaced proximally unless prevented by a braking surface area 41, whereby the spring 32 urges distally the rear wall 12 of the carrier 10 and proximally the slider 30.

The carrier 10 is provided with an opening 13 through which the braking surface area 41 acts on the slider 30. The brake mechanism or element comprises the brake lever 40 arranged on the spindle 2 and the braking surface area 41. The brake lever 40 consists of a long component 42 and a short component 43 forming an angle with the latter. Arranged in the angle between the short component 43 and the long component 42 of the brake lever 20 is the spindle 2. The long component 42 of the brake lever 40 is urged by a spring 50 such that the long component 42 is forced away from the pistol-type grip 20, resulting in the braking surface area 41 arranged on the short component 43 being urged against the slider 30 by the lever action, thus preventing a movement of the slider 30 in the proximal direction.

The slider 30 is configured such that a T-like plate 31 arranged at the distal end of the slider 30 protrudes through a longiudinal opening 11 in the plane carrier 10 and contacts the two plunger rods 6a, 6b at their distal end.

When the long component 42 of the brake lever 40 is pulled to the grip 20 against the force of the spring 50 the braking effect of the braking surface area 41 on the slider 30 is reduced so that the slider is shifted by the force of the spring 32 in the proximal direction, the plunger rods 6a, 6b, stopped by the T-piece 31, and the plungers 5a, 5b connected to the plunger rods being shifted in the proximal direction. This movement of the plungers 5a, 5b in the syringe bodies 4a, 5b results in the fluid being dispelled through the two outlet openings 9a, 9b and the cannulas 7a, 7b connected thereto.

To prevent accidental actuation of the brake lever a locking mechanism 60 is applied between the long component 42 of the brake lever 40 and the grip 20, this locking mechanism permits no movement of the brake lever 20 in the direction of the grip 20 in the closed position.

The accompanying Figures and this description depict and describe embodiments of the fluid delivery system of the present invention, and features and components thereof. Fastening, mounting, attaching or connecting the components of the present invention to form the apparatus or device as a whole, unless specifically described otherwise, are intended to encompass conventional fasteners such as machine screws, nut and bolt connectors, machine threaded connectors, snap rings, clamps such as screw clamps and the like, rivets, nuts and bolts, toggles, pins and the like. Components may also be connected by welding, friction fitting or deformation, if appropriate. Unless specifically otherwise disclosed or taught, materials for making components of the present invention are selected from appropriate materials such as metal, metallic alloys, fibers, plastics and the like, and appropriate manufacturing or production methods including casting, extruding, molding and machining may be used.

Any references herein to front and back, right and left, top and bottom, upper and lower and horizontal and vertical are intended for convenience of description only, not to limit the present invention or its components to any one positional or spatial orientation. Such terms are to be read and understood with their conventional meanings. In the Figures, elements common to the embodiments of the invention are commonly identified.

It is contemplated that various changes may be made without deviating from the spirit and scope of the present invention. Accordingly, it is intended that the scope of the present invention not be limited strictly to that of the above description of the present invention.

What is claimed is:

1. A generally pistol-shaped delivery device for simultaneously delivering fluids from two fluid containers equipped with plungers, comprising a grip, and an actuator, the actuator comprising two output elements, a push element which moves said output elements, a force element which acts on said push element in the direction of said fluid containers, and a brake element which cancels out the effect of said force element unless said brake element is modified manually.

2. The delivery device of claim 1, wherein said force element is a spring.

3. The delivery device of claim 1, wherein said brake element comprises a spring acting on a braking surface area.

4. The delivery device of claim 1, wherein said fluid containers are syringe bodies.

5. The delivery device of claim 4, wherein said syringe bodies are arranged in parallel.

6. The delivery device of claim 1, wherein said delivery device comprises a hollow carrier and a grip.

7. The delivery device of claim 6, wherein a spindle supporting a brake lever is generally and openly arranged between said grip and said hollow carrier.

8. The delivery device of claim 7, wherein said brake lever comprises a long component and a short component, whereby said long component and said short component form an angle with each other, and support a braking surface area.

9. The delivery device of claim 8, wherein a locking mechanism prevents accidental actuation of said brake lever.

10. The delivery device of claim 9, wherein said brake element comprises said brake lever, said spindle, said locking mechanism, said braking surface area, and a spring, whereby when said long component of said brake lever is urged away from said grip by the force of said spring, said braking surface area acts on said push element, and cancels out the effect of said force element.

11. The delivery device of claim 1, wherein said fluid containers are immovably held in place.

12. The delivery device of claim 1, further comprising a cannula fitted into an outlet opening of each fluid container, whereby mixing of the two fluids does not occur until they are at a site to which they are applied.

13. The delivery device of claim 12, further comprising a supporting housing which contains the cannulas.

14. The delivery device of claim 12, further comprising a squirter, whereby the two fluids to be mixed are squirted onto a surface area.

15. The delivery device of claim 1, wherein said push element comprises a slider and a T-shaped plate, arranged at a distal end of said slider, whereby said T-shaped plate contacts a distal end of said output elements.

16. The delivery device of claim 15, wherein a braking surface area in contact with said slider cancels out the effect of said force element.

17. A method of using a delivery device for simultaneously delivering fluids from two fluid containers equipped with plungers, comprising:

providing the two fluid containers equipped with plungers, each container holding a fluid to be mixed;

providing the delivery device, the delivery device being generally pistol-shaped, and comprising a grip and an actuator, the actuator comprising two output elements, a push element which moves said output elements, a force element which acts on said push element in the direction of said fluid containers, and a brake element acting on said push element, which cancels out the effect of said force element unless said brake element is modified manually;

attaching said fluid containers to said delivery device so that said plungers are in contact with said output elements;

providing a surface to apply the fluids to; and modifying said brake element, so that the effect of said force element is not cancelled, whereby said actuator forces fluid from an output end of the two fluid containers onto the surface.

18. The method of claim 17, whereby said braking element comprises a braking surface area which acts on said actuator to cancel out the effects of said force element, a brake lever, which carries said braking surface area, and a spring, attached to said brake lever, whereby the force of said spring holds said brake lever in a position where said braking surface area cancels out the effect of said force element.

19. The method of claim 17, wherein said force element is a spring.

20. The method of claim 17, wherein said push element comprises a slider and a generally T-shaped plate, arranged at a distal end of said slider, whereby said generally T-shaped plate contacts a distal end of said output elements.

21. A generally pistol-shaped delivery device for simultaneously delivering fluids from two fluid containers equipped with plungers, comprising a grip, and a generally hollow carrier, the carrier comprising two plunger rods, a slider, which moves said plunger rods, a spring which acts on said slider in the direction of said fluid containers, and a braking surface area acting on said slider, which cancels out the effect of said spring unless said brake braking surface area is modified manually.

22. The delivery device of claim 21, wherein said slider comprises a generally T-shaped plate arranged at a distal end of said slider, whereby said generally T-shaped plate contacts a distal end of said plunger rods.

23. The delivery device of claim 21, wherein, said generally hollow carrier is located on a generally central longitudinal axis.

24. The delivery device of claim 23, wherein said two fluid containers are each located on a longitudinal axis generally parallel to said generally central longitudinal axis of said generally hollow carrier.

25. The delivery device of claim 23, wherein said grip is located on a generally central longitudinal axis generally transverse to said generally central longitudinal axis of said generally hollow carrier.

26. The delivery device of claim 21, wherein said grip and said generally hollow carrier are generally perpendicular.

* * * * *